Figure 1:
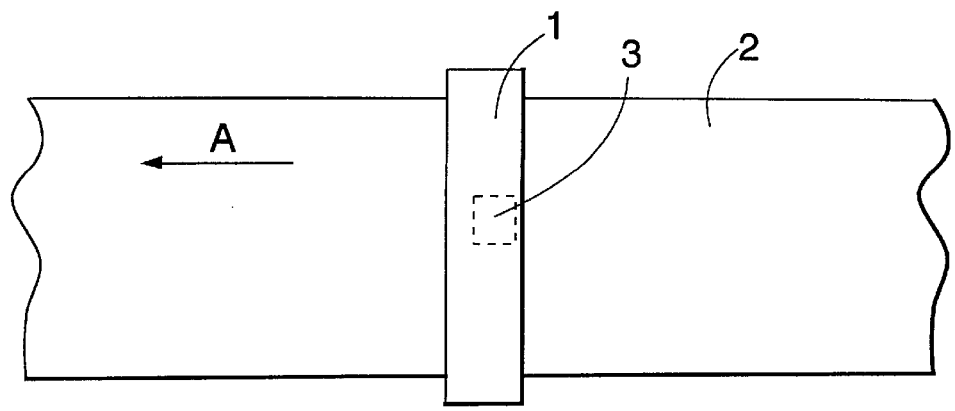

United States Patent [19]
Shakespeare

[11] Patent Number: 5,943,906
[45] Date of Patent: Aug. 31, 1999

[54] METHOD FOR OPERATING A TRAVERSING SENSOR APPARATUS

[75] Inventor: John Shakespeare, Siuro, Finland

[73] Assignee: Valmet Automation Inc., Helsinki, Finland

[21] Appl. No.: 08/928,537

[22] Filed: Sep. 12, 1997

[51] Int. Cl.⁶ .................................................. G01L 5/04
[52] U.S. Cl. .............................................................. 73/159
[58] Field of Search ..................... 73/73, 159; 162/198, 162/253, 258, 259, 263; 364/471; 356/238, 429, 430, 431; 250/252.1, 563

[56] References Cited

U.S. PATENT DOCUMENTS

| | | | |
|---|---|---|---|
| 4,939,929 | 7/1990 | Östman | 73/159 |
| 5,022,966 | 6/1991 | Hu | 162/198 |
| 5,298,122 | 3/1994 | Munch et al. | 162/259 |
| 5,493,910 | 2/1996 | Hall et al. | 73/159 |
| 5,714,692 | 2/1998 | Rohde | 73/159 |

*Primary Examiner*—William Oen
*Attorney, Agent, or Firm*—Ladas & Parry

[57] ABSTRACT

Method for operating a traversing sensor apparatus, wherein the properties of a paper web are measured through traversing such that a measuring head is moved during the measurement in the cross-machine direction. The movement of the measuring head in the cross-machine direction is stopped above the paper web and data is collected for a certain period through measurement from an area narrower than the width of the paper web, whereafter the movement of the measuring head in the cross-machine direction is continued. The data collected from an area narrower than the width of the paper web is used to calculate MD and CD values and to determine the effect of harmonic variations.

8 Claims, 1 Drawing Sheet

METHOD FOR OPERATING A TRAVERSING SENSOR APPARATUS

The invention relates to a method for operating a traversing sensor apparatus, in which method the properties of a moving web are measured through traversing such that a measuring head is moved during the measurement in the cross-machine direction.

A traversing array of sensors is commonly used to measure properties of a moving web during manufacture, especially in the paper industry. The direction of traverse is normally substantially perpendicular to the direction of movement of the web. The sensors therefore measure properties of diagonal samples of the web, rather than the whole web. Measurements are made at substantially the same plurality of locations across the machine during each traverse, and they may be made while traversing the web in one or both directions.

Measured variations in properties of the web of interest to the manufacturer are commonly separated by means of numerical algorithms into estimates of the machine direction (MD) and cross-machine direction (CD) variations. The usual separation methods attempt to identify MD variations and to separate them from the scan data, and the remaining variations are considered to be CD and random variations.

MD variations which are high frequency cannot be separated and are commonly deemed to be random variations. Variations designated as random are often removed by filtering. MD variations which are low frequency may be substantially identified and separated with any of several numerical algorithms. Such algorithms include averaging, exponential filtering, or Kalman filtering applied to each cell.

However, when MD variations occur with a period which is a harmonic of the traverse time of the scanner, filtering techniques are no longer effective, as the variation may be unobservable. This happens especially when the MD variation is both harmonic and in phase with the traverse. A phase-shifted harmonic MD variation exhibits reduced observability to filtering techniques. MD variations which are not exactly harmonic but which are close to harmonic with the traverse time are visible only after long identification periods during which the process is stationary.

U.S. Pat. Nos. 4,939,929 and 5,298,122 disclose a measuring method where the idle time of the measuring head outside the edge of the web and/or the speed at which the measuring head crosses the web during different traverses are altered randomly. In such a manner, it is possible to avoid or vary periodicity in the movement of the measuring head and therefore to eliminate such errors that would occur when the changes take place in an interval that is harmonic with the traverse time of the measuring head. However, it is not possible to determine the frequency of variations in this manner, and when these methods are used it is only possible to hope that the changes caused randomly in the movement of the measuring head eliminate the problem.

The purpose of the present invention is to provide a method with which the measuring accuracy can be improved.

The method according to the invention is characterized in that the movement of the measuring head in the cross-machine direction is stopped above the moving web and the properties of the moving web are measured for a certain period from an area narrower than the width of the moving web, whereafter the movement of the measuring head in the cross-machine direction is continued and the data collected from an area narrower than the width of the moving web is used to calculate MD and CD values and to determine the effect of harmonic variations.

The basic idea of the invention is that the properties of a moving web are measured through traversing so that the measuring head is moved during the measurement in the cross-machine direction, and that the movement of the measuring head in the cross-machine direction is stopped and data is collected through measurement for a certain period from an area that is narrower than the width of the moving web, and the movement of the measuring head in the cross-machine direction is thereafter continued, not necessarily in the same manner as before stopping. The scan speed or direction, for example, may be different after the stoppage. The data collected from an area narrower than the width of the moving web is used to calculate MD and CD values and to determine the effect of the harmonic variations. The idea of a preferred embodiment is that the data collected from an area narrower than the width of the moving web is used to determine for the movement of the measuring head in the cross-machine direction a certain speed with which the effect of the harmonic variations is the smallest. The idea of another preferred embodiment is that the measuring head is kept substantially stationary for a certain period after the stopping. The idea of a third preferred embodiment is that after the measuring head has been stopped, it traverses for a certain period in an area that is narrower than the width of the moving web.

The invention has the advantage that when the movement of the measuring head in the cross-machine direction is stopped, the effect of such MD variations that are harmonic with the speed of motion of the measuring head can be identified, thus enabling a suitable controller to eliminate or regulate them. Further, when the measurement is carried out for a certain period from an area narrower than the width of the moving web, it is possible to determine accurately the variations in the machine and cross-machine direction and the effect of the harmonic variations. It is also possible to determine for the measuring head a new speed with which the effect of the harmonic variations is small, so that the measuring accuracy subsequent to the stopping can be improved.

The term moving web relates in this connection for example in a moving paper, board or tissue web during manufacture and also other web or sheet materials such as shingle, ceiling tiles, plastic sheet or metal sheet.

Figure 2:
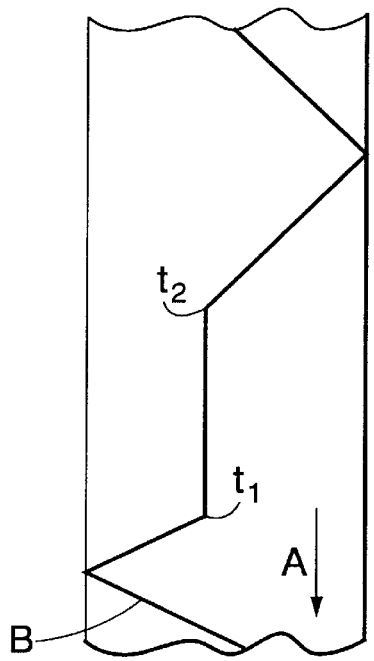
Figure 3:
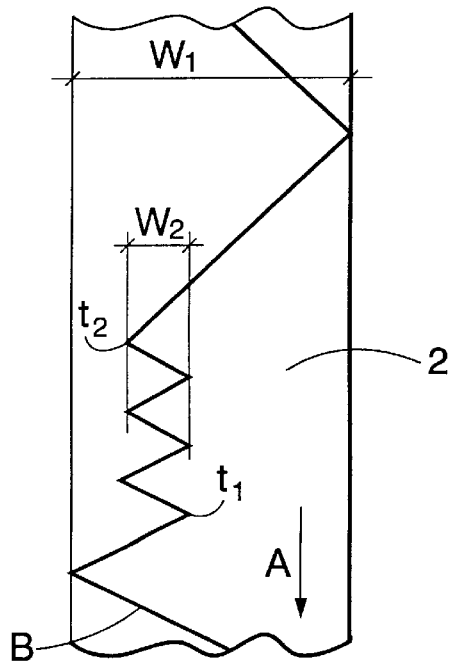

The invention will be described in greater detail in the accompanying drawing, in which FIG. 1 is a schematic top view of a measuring apparatus for measuring the properties of a paper web, FIG. 2 shows schematically the principle of a measuring method according to the invention, and FIG. 3 shows schematically another principle of the measuring method according to the invention.

FIG. 1 shows a stationary measuring frame 1. A paper web 2 is arranged to move in the direction of arrow A. The measuring frame 1 is provided with a measuring head 3, denoted with a broken line in FIG. 1, such that the measuring head 3 reciprocates transversely to the direction of travel of the paper web 2. The arrangement for measuring the properties of a paper web 2 is known per se for a person skilled in the art and therefore it is not described in greater detail in this connection.

FIG. 2 shows a polyline B that describes the position of the measuring head above the paper web 2 as the web moves in the direction of arrow A. The measuring head measures the properties of the paper web 2 substantially continuously. The movement of the measuring head in the cross-machine direction is stopped at the paper web 2 at moment $t_1$. The measuring head is thereafter kept substantially stationary until moment $t_2$. The measurement in the interval $t_1$ to $t_2$ therefore takes place along a line substantially parallel to the machine direction. In the interval $t_1$ to $t_2$, measurements are carried out and data is collected about the properties of the paper web 2, and this data is used to calculate the MD and CD values of the paper web and to determine the effect of the harmonic variations. After moment $t_2$, the movement of the measuring head across the paper web 2 continues. On the basis of the data collected in the interval $t_1$ to $t_2$, it is possible to determine the speed with which the effect of the harmonic variations on the measuring accuracy is the smallest. In the case shown in FIG. 2, the speed of the measuring head during the traversing of the paper web 2 has been changed such that before moment $t_1$ the speed of the measuring head is greater than after moment $t_2$. The new speed is set to an optimal value on the basis of the collected data, and the measurement result is therefore more accurate and reliable after moment $t_2$.

The arrangement shown in FIG. 3 corresponds mainly to FIG. 2, but in the situation shown in FIG. 3 at moment $t_1$ when the movement of the measuring head in the cross-machine direction is stopped over the paper web 2, the measuring head is not kept stationary but it is arranged to traverse in a subtraversing area $W_2$ that is narrower than the width $W_1$ of the paper web 2. Traversing is continued in this narrower subtraversing area $W_2$ until moment $t_2$. Data is collected in the interval $t_1$ to $t_2$ in a similar manner as in FIG. 2 and the collected data can be naturally utilized as in FIG. 2. The difference is that in the case shown in FIG. 3 the data is collected from a wider area than in the case shown in FIG. 2, but it is naturally only collected from the subtraversing area $W_2$ that is narrower than the width $W_1$ of the paper web 2. In this manner, it is possible to eliminate the effect of the harmonic variations and to use the collected data to calculate the MD and CD values. Furthermore, the collected data is also more reliable than in the case shown in FIG. 2, since for example a longitudinal error situated at one point in the cross-machine direction cannot have a harmfully great effect on the result of the measurement carried out as shown in FIG. 3.

The drawing and the related description are only intended to illustrate the inventive idea. The details of the invention may vary within the scope of the claims. Therefore, in the simplest form the interval $t_1$ to $t_2$ may recur regularly, but in order to increase the measuring accuracy the length and frequency of occurrence of the interval $t_1$ to $t_2$ can also be varied randomly, or can be determined by other events, such as a grade change or significant change in machine speed or other designated process variables. Further, keeping the measuring head stationary in the cross-machine direction or traversing in an area narrower than the width of the paper web 2 can also be implemented more than once as the measuring head moves across the paper web 2. Also, the measuring head can be stopped for a desired period outside the edge of the paper web 2. Further the direction of motion of the measuring head in the cross-machine direction can be changed during the web traverse. The measurement data can be analysed for example by means of averaging, exponential filtering or Kalman filtering or some other algorithm suitable for the purpose as it is known for a person skilled in the art.

I claim:

1. A method for operating a traversing sensor apparatus, in which method the properties of a moving web are measured through traversing so that a measuring head is moved during the measurement in the cross-machine direction, and the movement of the measuring head in the cross-machine direction is stopped above the moving web and the properties of the moving web are measured for a certain period from an area narrower than the width of the moving web, whereafter the movement of the measuring head in the cross-machine is continued and the data collected from an area narrower than the width of the moving web is used to calculate MD and CD values and to determine the effect of harmonic variations.

2. A method according to claim 1, wherein the speed of motion of the measuring head in the cross-machine direction is changed during the moving web traverse.

3. A method according to claim 1, wherein the data collected from an area narrower than the width of the moving web is used to determine for the movement of the measuring head in the cross-machine direction a certain speed with which the effect of the harmonic variations is small.

4. A method according to claim 3, wherein the speed of the measuring head in the cross-machine direction is changed during the moving web traverse.

5. A method according to claim 1, wherein the measuring head is kept substantially stationary for a certain period after the movement in the cross-machine direction has been stopped.

6. A method according to claim 1, wherein after the measuring head has been stopped, it traverses for a certain period in a subtraversing area narrower than the width of the moving web.

7. A method according to claim 1, wherein the direction of motion of the measuring head in the cross-machine direction is changed during the web traverse.

8. A method according to claim 1, wherein the moving web is a paper web.

* * * * *